United States Patent
Barajas-Torres et al.

(10) Patent No.: US 10,441,420 B2
(45) Date of Patent: Oct. 15, 2019

(54) DEVICES AND METHODS FOR TRANSCATHETER VALVE LOADING AND IMPLANTATION

(71) Applicant: Medtronic Vascular, Inc., Santa Rosa, CA (US)

(72) Inventors: Martha Barajas-Torres, Santa Rosa, CA (US); Kevin Mauch, Windsor, CA (US); Jeffrey Sandstrom, Scandia, MN (US); Jill Mendelson, San Francisco, CA (US); Don Tran, Novato, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 190 days.

(21) Appl. No.: 15/376,739

(22) Filed: Dec. 13, 2016

(65) Prior Publication Data
US 2017/0165067 A1 Jun. 15, 2017

Related U.S. Application Data

(60) Provisional application No. 62/267,200, filed on Dec. 14, 2015.

(51) Int. Cl.
*A61F 2/24* (2006.01)
*A61F 2/95* (2013.01)

(52) U.S. Cl.
CPC .......... *A61F 2/2439* (2013.01); *A61F 2/2415* (2013.01); *A61F 2/2418* (2013.01); *A61F 2002/9511* (2013.01)

(58) Field of Classification Search
CPC ...... A61F 2/95–97; A61F 2/2427–2439; A61F 2/01–013; A61F 2002/9505–9665; A61F 2002/011–018
See application file for complete search history.

(56) References Cited

U.S. PATENT DOCUMENTS

| | | |
|---|---|---|
| 5,035,706 A | 7/1991 | Giantureo et al. |
| 5,693,084 A | 12/1997 | Chuter |
| 5,776,186 A | 7/1998 | Uflacker |
| 6,280,465 B1 | 8/2001 | Cryer |
| 6,517,550 B1 | 2/2003 | Konga et al. |
| 6,733,521 B2 | 5/2004 | Chobotov et al. |
| 6,740,111 B1 | 5/2004 | Lauterjung |
| 7,033,390 B2 | 4/2006 | Johnson et al. |
| 7,329,275 B2 | 2/2008 | Yee |
| 7,503,929 B2 | 3/2009 | Johnson et al. |

(Continued)

FOREIGN PATENT DOCUMENTS

| | | |
|---|---|---|
| EP | 1842508 A1 | 10/2007 |
| WO | WO2007/130881 | 11/2007 |
| WO | WO2014/144247 | 9/2014 |

OTHER PUBLICATIONS

U.S. Appl. No. 62/117,013, filed Feb. 17, 2015, Duffy et al.

(Continued)

*Primary Examiner* — Jonathan A Hollm

(57) ABSTRACT

The present disclosure relates to numerous devices and methods for transcatheter stented prosthetic heart valve loading and delivery. Such devices and methods reduce suture tangling and also provide the ability to adjust the stented prosthetic heart valve expansion and contraction prior to the final release of the stented prosthetic heart valve from the delivery device.

16 Claims, 11 Drawing Sheets

(56) References Cited

U.S. PATENT DOCUMENTS

| | | |
|---|---|---|
| 8,403,981 B2 | 3/2013 | Forster et al. |
| 2005/0119722 A1 | 6/2005 | Styrc et al. |
| 2005/0137687 A1 | 6/2005 | Salahieh et al. |
| 2007/0100427 A1 | 5/2007 | Perouse |
| 2007/0233223 A1* | 10/2007 | Styrc .................. A61F 2/2439 623/1.11 |
| 2008/0147183 A1* | 6/2008 | Styrc .................. A61F 2/2418 623/2.12 |
| 2009/0048656 A1 | 2/2009 | Wen |
| 2010/0249915 A1 | 9/2010 | Zhang |
| 2010/0286768 A1 | 11/2010 | Alkhatib |
| 2011/0040366 A1 | 2/2011 | Goetz et al. |
| 2011/0106246 A1 | 5/2011 | Malewicz et al. |
| 2012/0277734 A1 | 11/2012 | Goetz et al. |
| 2013/0245752 A1 | 9/2013 | Goetz et al. |
| 2013/0338755 A1 | 12/2013 | Goetz et al. |
| 2014/0249622 A1* | 9/2014 | Carmi .................. A61F 2/2442 623/2.11 |
| 2014/0330368 A1 | 11/2014 | Gloss et al. |
| 2015/0112430 A1 | 4/2015 | Creaven et al. |
| 2015/0238315 A1 | 8/2015 | Rabito et al. |
| 2015/0265442 A1* | 9/2015 | Styrc .................. A61F 2/2436 623/1.11 |

OTHER PUBLICATIONS

PCT/US2016/066313, The International Search Report and The Written Opinion of the International Searching Authority, dated Apr. 6, 2017.

PCT/US2016/066323, The International Search Report and the Written Opinion of the International Searching Authority, dated Nov. 8, 2017.

* cited by examiner

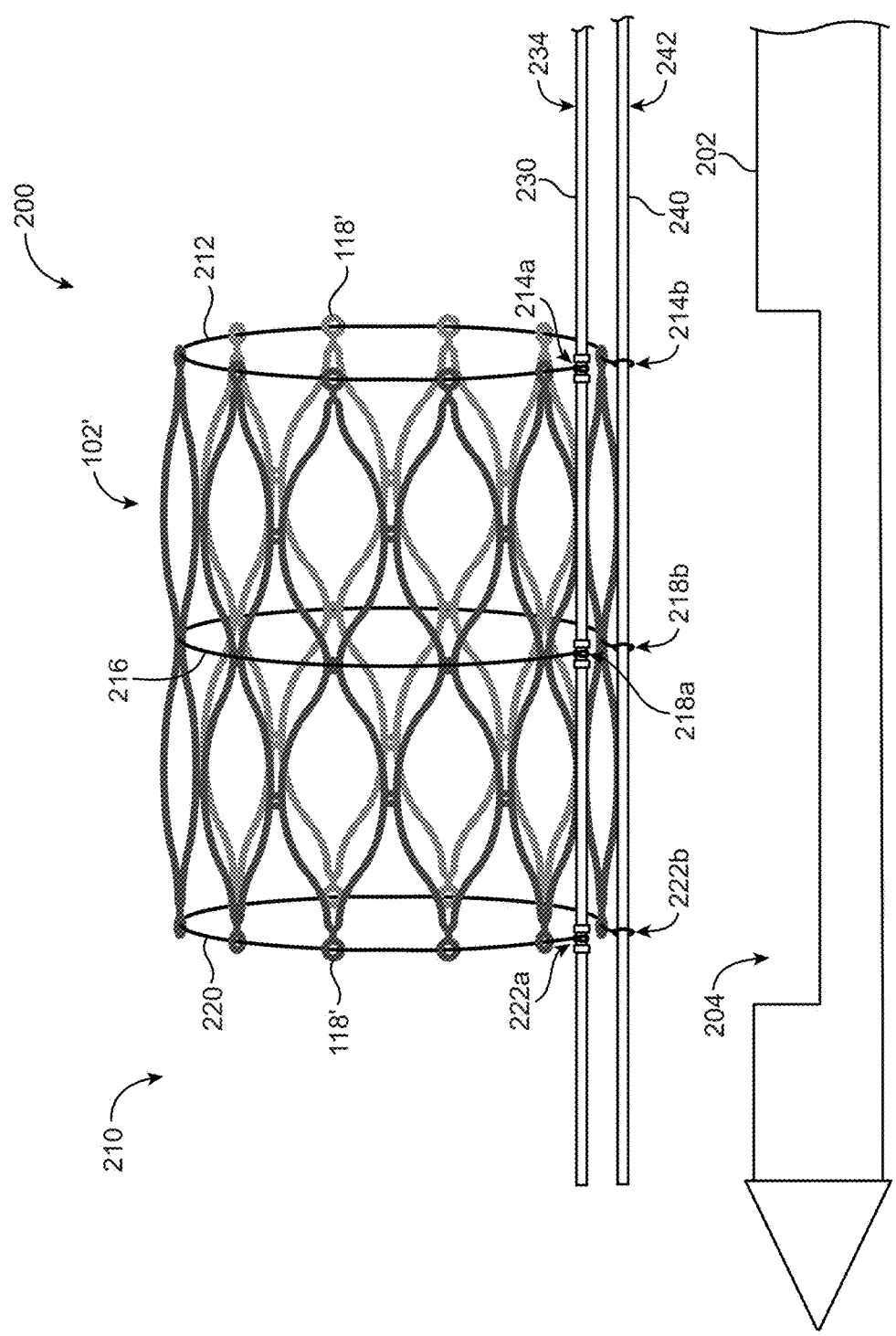

DEVICES AND METHODS FOR TRANSCATHETER VALVE LOADING AND IMPLANTATION

CROSS-REFERENCE TO RELATED APPLICATIONS

This Non-Provisional Patent Application claims the benefit of the filing dates of U.S. Provisional Patent Application Ser. No. 62/267,200, filed Dec. 14, 2015, entitled "Devices and Methods for Transcatheter Valve Loading and Implantation," which is herein incorporated by reference.

BACKGROUND

The disclosure relates to delivery devices and methods for transcatheter stented prosthetic heart valve loading and implantation.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. With these delivery devices, the valved stent is crimped down to a desired size and held in that compressed state within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a prosthetic valve is disclosed in U.S. Pat. No. 5,957,949 to Leonhardt et al., which is incorporated by reference herein in its entirety.

The actual shape and configuration of any particular transcatheter prosthetic heart valve is dependent, at least to some extent, upon the valve being replaced or repaired (e.g., mitral valve, tricuspid valve, aortic valve, or pulmonary valve). The stent frame must oftentimes provide and maintain (e.g., elevated hoop strength and resistance to radially compressive forces) a relatively complex shape in order to achieve desired fixation with the corresponding native anatomy. Taken in combination, these design features can give rise to delivery obstacles. For example, when compressed and constrained within the delivery device's outer sheath capsule, a self-expanding stent frame will exert significant radial forces on the capsule. Thus, the capsule must have a robust construction, capable of statically resisting the applied force. However, the capsule, as well as other portions of the outer sheath, must also be sufficiently flexible to traverse the tortuous path leading to the native valve annulus site. As a point of reference, the preferred delivery approach oftentimes includes one or more significant bends or turns. In many instances, the native anatomy creates the "tight" or small radius of curvature bends; as the capsule (or other components of the delivery device) comes into atraumatic contact with the native anatomy, the native anatomy naturally assists in "forcing" the outer sheath (including the capsule) to the necessary shape. A retrograde approach to the aortic valve is but one example, where contact with the native anatomy assists in directing the delivery device about the significant curvature of the aortic arch.

The present disclosure addresses problems and limitations with the related art.

SUMMARY

The present disclosure relates to numerous delivery devices and methods for transcatheter stented prosthetic heart valve ("prosthetic valve") loading and implantation. Such delivery devices can include an optional outer delivery sheath assembly, an inner shaft assembly and a handle assembly. The delivery device provides a loaded delivery state in which the prosthetic valve is loaded and compressed over the inner shaft assembly. The compression on the prosthetic valve is adjustable with one or more sutures. The delivery device is configured to permit the prosthetic valve to self-expand and partially release from the inner shaft assembly.

Certain aspects of the disclosure are directed to delivery devices and methods for positioning a prosthetic valve in a compressed state for delivery and, subsequently, an expanded state for deployment at a native aortic heart valve. Such delivery devices are arranged and configured such that a plurality of sutures generally encircle the prosthetic valve. Each suture has two ends; wherein one end is fixedly secured to a wire and the second end is releasably secured to a release pin. Both the wire and the release pin are positioned within a spindle of the delivery device. When the wire is pulled away from the prosthetic valve in a proximal direction, the sutures are tensioned to place the prosthetic valve in a compressed state for delivery though a patient's vasculature. To deploy the prosthetic valve, the tension is released by moving the wire in a distal direction. As desired, the sutures can be re-tensioned to compress the prosthetic valve for repositioning. At the site of implantation, the release pin is pulled in a proximal direction to disengage the second ends of the sutures from the release pin. The delivery device, including the wire, release pin and sutures, is then withdrawn from the patient.

Some aspects of the disclosure are directed toward alternate methods and delivery devices for loading a prosthetic valve to a catheter delivery device with sutures. In one such embodiment, a suture engagement member is positioned within the catheter and the suture engagement member engages at least one suture. The suture engagement member is then retracted proximally within the catheter, thus pulling the sutures proximally, to compress the prosthetic valve. To release compression and disengaged from the suture(s), the engagement member is pushed distally. The suture engagement member can take a variety of configurations suitable for engaging and disengaging the sutures.

BRIEF DESCRIPTION OF THE DRAWINGS

FIG. 5A is a partial, schematic view of a delivery device for the delivery of a stented prosthetic heart valve before a suture assembly is secured to a spindle of the delivery device (only the stent frame of the stented prosthetic heart valve is shown for ease of illustration).

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to a stented prosthetic heart valve, the terms "distal" and "outflow" are understood to mean downstream to the direction of blood flow, and the terms "proximal" or "inflow" are understood to mean upstream to the direction of blood flow. Although the present disclosure has been described with reference to preferred embodiments, workers skilled in the art will recognize that changes can be made in form and detail without departing from the spirit and scope of the present disclosure.

Figure 1:
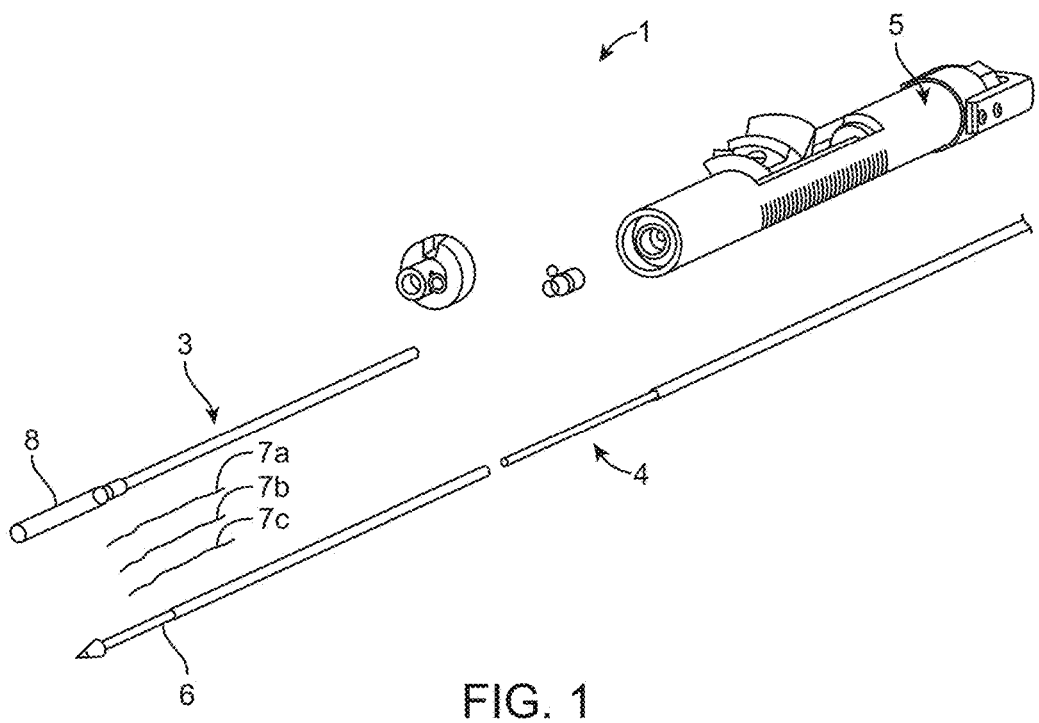
FIG. 1 is a perspective view of a delivery device for delivering a stented prosthetic heart valve.
Figure 2A:
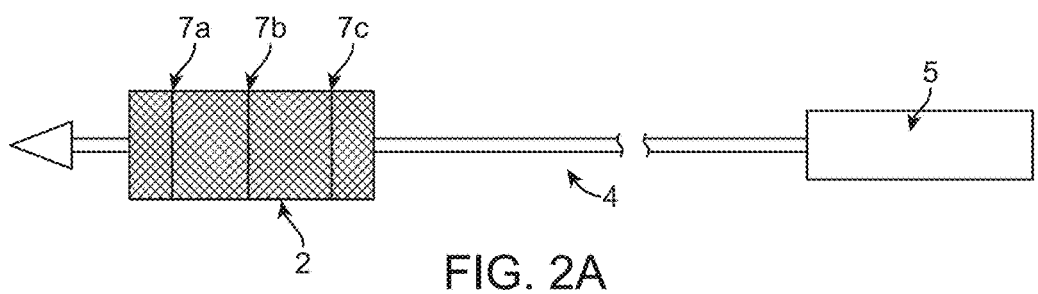
FIG. 2A is a partial, schematic illustration of the delivery device of FIG. 1 having a stented prosthetic heart valve positioned over an inner shaft assembly; the stented prosthetic heart valve shown in an expanded state.
Figure 2B:
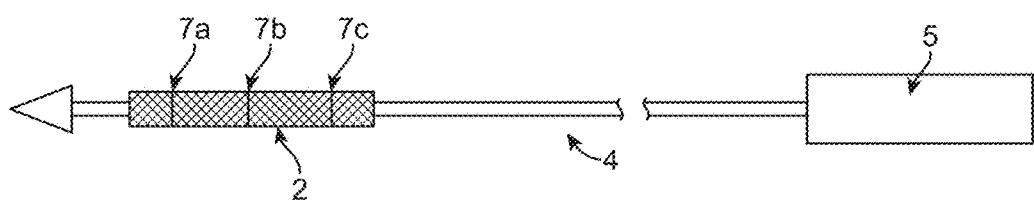
FIG. 2B is a schematic illustration of the delivery device of FIG. 2A having the stented prosthetic heart valve positioned over the inner shaft assembly; a plurality of sutures compressing the stented prosthetic heart valve into a compressed state.

As described below, aspects of the present disclosure relate to delivery devices utilizing one or more sutures to retain the stented prosthetic heart valve ("prosthetic valve") in a compressed state during delivery to a target site. The suture related features of the present disclosure are useful with a variety of different delivery devices configurations. By way of background, general components of one non-limiting example of a delivery device 1 with which the present disclosures are useful are illustrated in FIGS. 1-2B. The delivery device 1 is arranged and configured for percutaneously delivering a prosthetic valve 2 to a patient's defective heart valve. The delivery device 1 includes an optional outer delivery sheath assembly 3, an inner shaft assembly 4, and a handle assembly 5. One or more sutures 7a-7c (schematically depicted) are provided, and can be considered part of the delivery device 1 in some embodiments or as part of the prosthetic valve 2 in other embodiments. The delivery device 1 provides a loaded delivery state in which the prosthetic valve 2 is loaded over the inner shaft assembly 4 and is compressively retained on a spindle 6 or the like by the sutures 7a-7c. As is schematically illustrated in FIGS. 2A-2B, the compression on the prosthetic valve 2 can be adjusted with one or more sutures 7a-c. Once the loaded and compressed prosthetic valve 2 is located at a target site, tension in the sutures 7a-7c is lessened or released to permit the prosthetic valve 2 to self-expand, partially releasing and ultimately fully deploying the prosthetic valve 2 from the inner shaft assembly 4. In the illustrated embodiment, the optional delivery sheath assembly 3, where provided, includes a capsule 8, selectively disposed over the prosthetic valve 2 that assists in constraining the prosthetic valve 2 in the loaded or compressed state and can be retracted by the handle assembly 5 to expose the prosthetic valve 2. The present disclosure focuses on numerous devices and methods for prosthetic valve loading and implantation using a delivery device, such as the delivery device 1. Such delivery devices utilize sutures for adjustably compressing and releasing said compression on the prosthetic valve either for loading or readjusting the position of a partially-deployed prosthetic valve.

As referred to herein, prosthetic valves useful with the various devices and methods of the present disclosure may assume a wide variety of configurations, such as a bioprosthetic heart valve having tissue leaflets or a synthetic heart valve having polymeric, metallic or tissue-engineered leaflets, and can be specifically configured for replacing valves of the human heart. The prosthetic valves of the present disclosure may be self-expandable, for example. In general terms, the prosthetic valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed condition to a normal, radially expanded condition. The struts or wire segments can be formed from a shape memory material, such as a nickel titanium alloy (e.g., Nitinol™). Further, the stent frame can be laser-cut from a single piece of material, or can be assembled from a number of discrete components.

Figure 3:
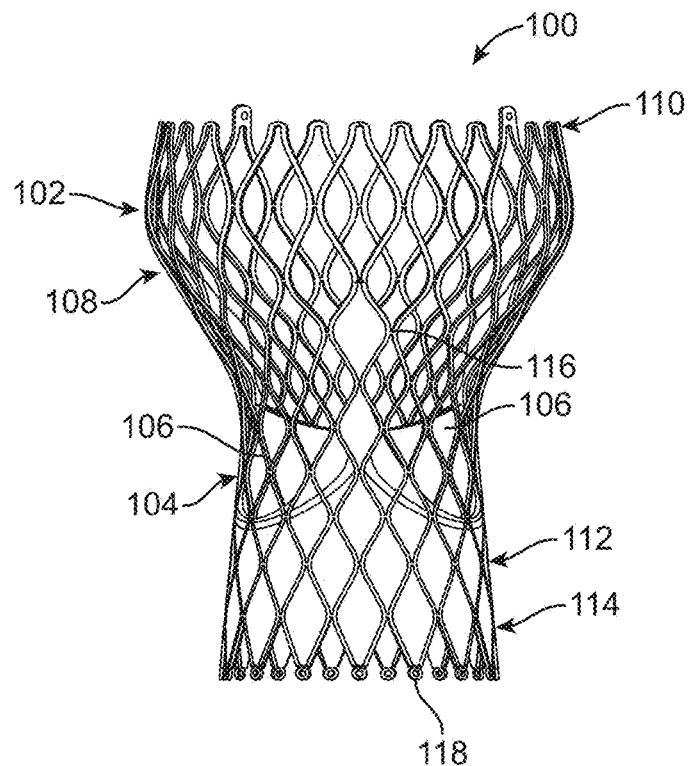
FIG. 3 is a front view of a stented prosthetic heart valve that can be used with the delivery devices disclosed herein.

One simplified, non-limiting example of a prosthetic valve 100 is illustrated in FIG. 3. As a point of reference, the prosthetic valve 100 is shown in a normal or expanded state in the view of FIG. 3. The prosthetic valve 100 includes a stent or stent frame 102 and a valve structure 104. The stent frame 102 can assume any of the forms mentioned above, and is generally constructed to be self-expandable from the compressed state to the normal, expanded state.

The valve structure 104 of the prosthetic valve 100 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 104 can be formed, for example, from bovine, porcine, equine, ovine and/or other suitable animal tissues. In some embodiments, the valve structure 104 can be formed, for example, from heart valve tissue, pericardium, and/or other suitable tissue. In some embodiments, the valve structure 104 can include or form one or more leaflets 106. For example, the valve structure 104 can be in the form of a tri-leaflet bovine pericardium valve, a bi-leaflet valve, or another suitable valve.

In some prosthetic valve constructions, such as that of FIG. 3, the valve structure 104 can comprise two or three leaflets that are fastened together at enlarged lateral end regions to form commissural joints, with the unattached edges forming coaptation edges of the valve structure 104. The leaflets 106 can be fastened to a skirt that in turn is attached to the stent frame 102. The prosthetic valve 100 includes an outflow portion 108 corresponding to a first or outflow end 110 (forcing out fluid) of the prosthetic valve 100. The opposite end of the prosthetic valve 100 can define an inflow portion 112 corresponding to a second or inflow end 114 (receiving fluid) of the prosthetic valve 100. As shown, the stent frame 102 can have a lattice or cell-like structure, and optionally forms or provides posts 116 corresponding with commissures of the valve structure 104 as well as eyelets 118 (or other shapes; only a select few are labeled) at the outflow and inflow ends 110, 114. If provided, the posts 116 are spaced equally around frame 102 (only one post 116 is clearly visible in FIG. 3).

Figure 4:
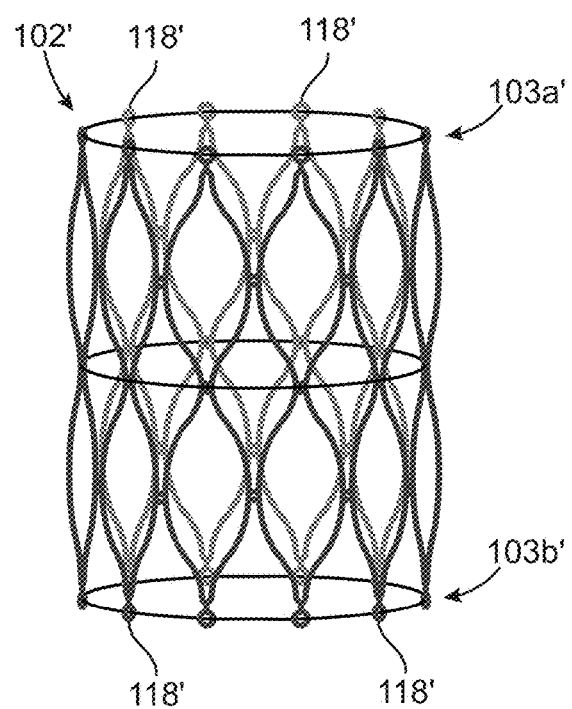
FIG. 4 is a perspective view of an alternate stented prosthetic heart valve frame configuration.

One alternative stent frame 102' is illustrated in FIG. 4. The stent frame 102' is shown in an expanded state and has a proximal end 103a' and a distal end 103b' as well as a plurality of eyelets 118' (only a select few are labeled) spaced equally around the stent frame 102'. It will be understood that the stent frame 102' can be used with the valve structure 104 of FIG. 3. It will be understood that the valve structure 104 of FIG. 3 can be used with the stent frame 102' of FIG. 4.

Figure 5B:
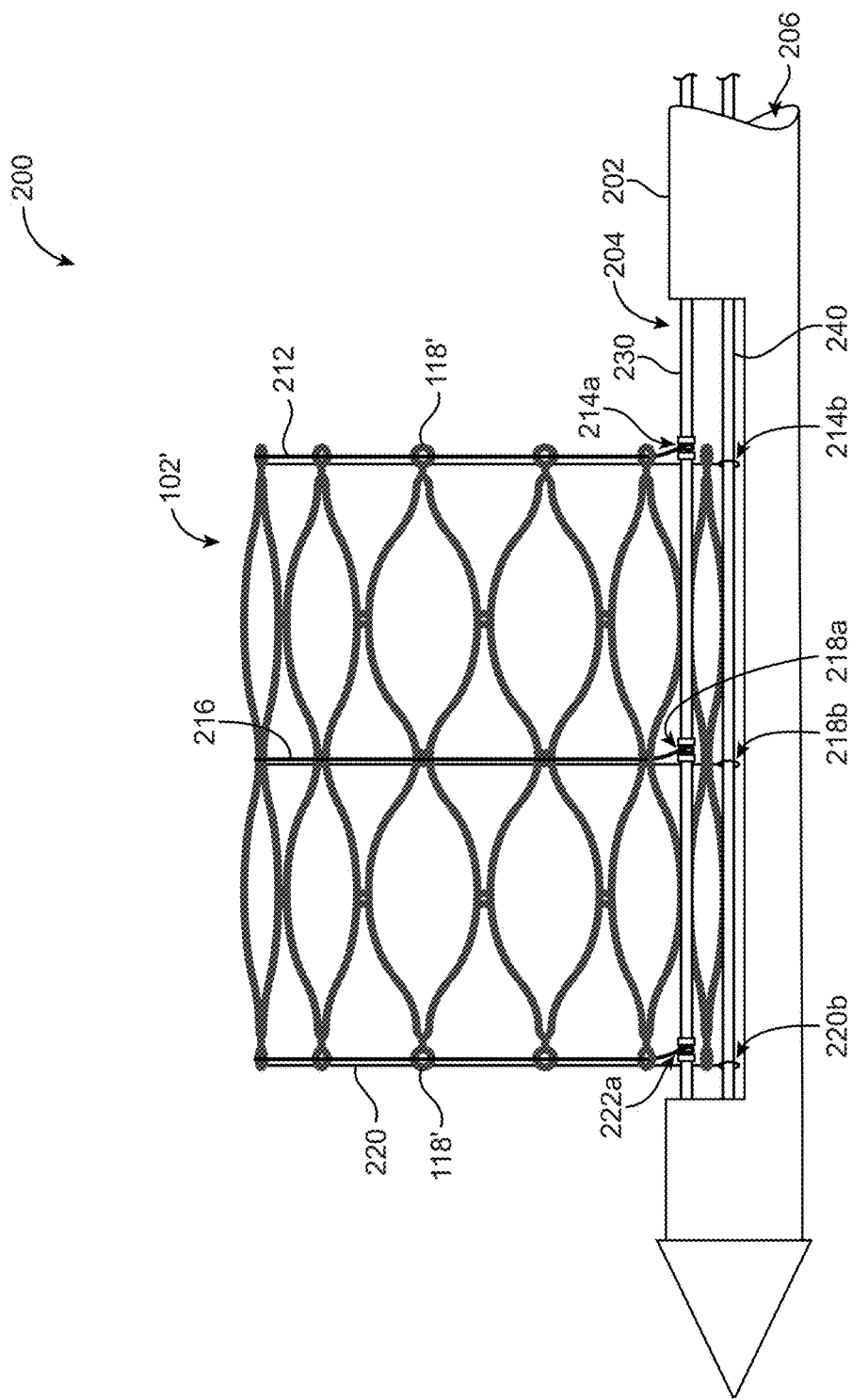
FIG. 5B is a partial, schematic view of the suture assembly of FIG. 5A partially positioned within a lumen of the spindle.
Figure 5C:
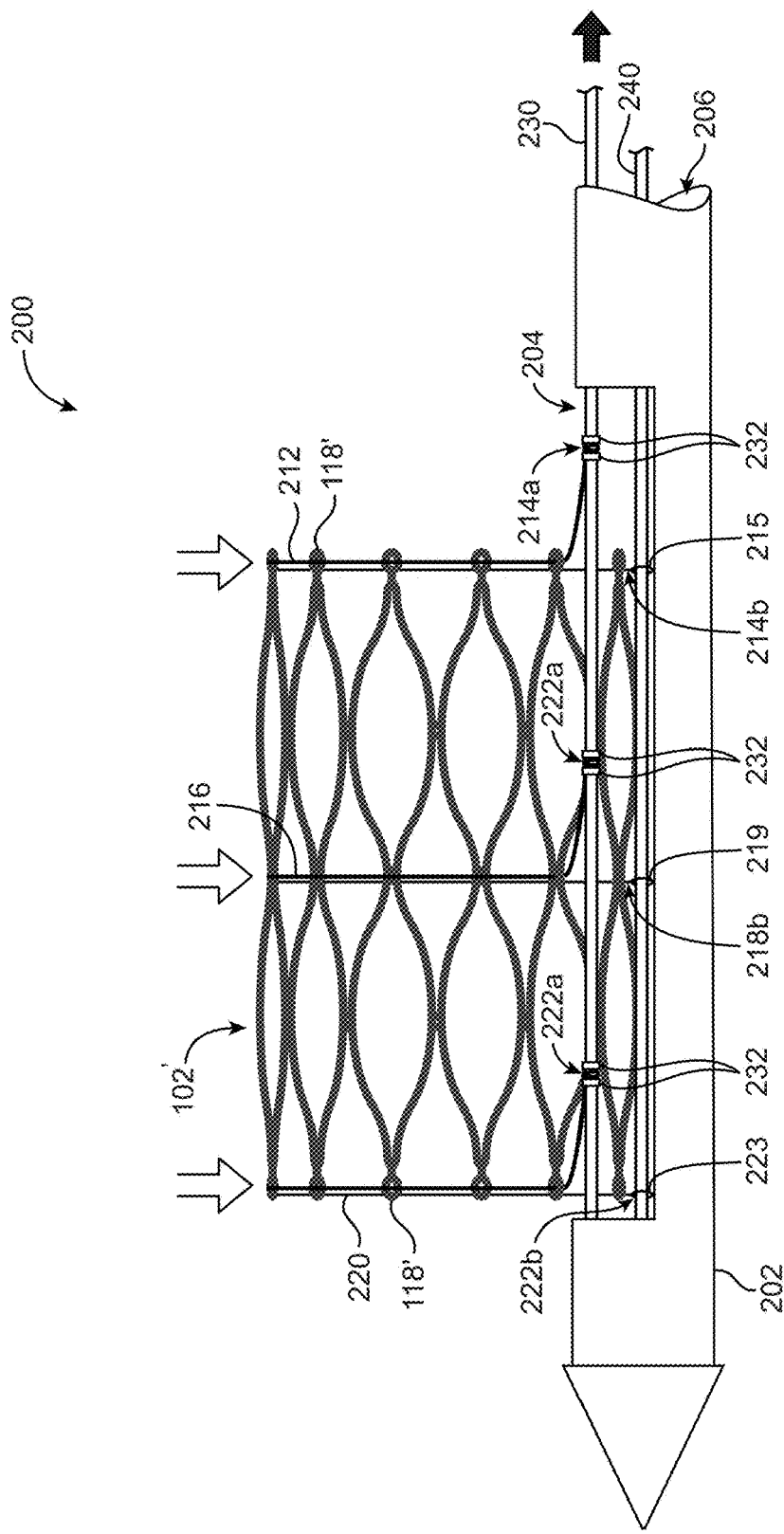
FIG. 5C is a partial, schematic view of the delivery device of FIGS. 5A-5B illustrating how three sutures are secured to a wire and also a release pin, both of which have been inserted into the lumen of the spindle.

FIGS. 5A-5C illustrate select portions of a delivery device 200 for releasably securing the prosthetic valve to an inner shaft assembly 202 of the delivery device 200 that can be substituted for the inner shaft assembly 4 (only part of the delivery device 200 is shown, see also FIG. 1 and related disclosure; in addition, only the stent frame 102' of the prosthetic valve is shown for ease of illustration). As generally illustrated in FIG. 5A, the delivery device 200 can include a sub assembly 210 including one proximal suture 212, one intermediate suture 216, one distal suture 220, a wire 230 and a release pin 240. The sutures 212, 216, 220 are all of approximately the same length so that they compress the stent frame 102' uniformly in the state of FIG. 5A. In example embodiments, the sutures 212, 216, 220 can be threaded though eyelets 118' or through stent frame 102' to maintain the lateral position of the respective suture 212, 216, 220. Each suture 212, 216, 220 includes first and second ends 214a-b, 218a-b, 222a-b. The first end 214a, 218a, 222a of each of the sutures 212, 216, 220 is fixedly secured to the wire 230, for example, by adhering the suture 212, 216, 220 to the wire 230 or tying. If the suture 212, 216, 220 is tied to the wire 230, it may be desirable to include one or more position stabilizers 232 on the wire 230 to generally maintain the lateral position of the respective suture 212, 216, 220 on the wire 230. Alternatively, apertures (not shown) can be formed in the wire 230 through which the sutures 212, 216, 220 can be tied. The second end 214b, 218b, 222b of each of the sutures 212, 216, 220 forms a loop 215, 219, 223 positioned around the release pin 240. The sutures 212, 216, 220 are woven or otherwise disposed around the circumference of the stent frame 102' and are tensioned to compress the prosthetic valve in a loaded, compressed state such that it can be delivered to the defective heart valve via the patient's vascular system.

Once the sub assembly 210 is prepared, as is schematically illustrated in FIG. 5A, the wire 230 and release pin 240 can be inserted through a slot 204 in the inner shaft assembly 202 that provides access to an interior lumen 206 of the inner shaft assembly 202 as shown in FIG. 5B. A proximal end 234 of the wire 230 and a proximal end 242 of the release pin 240 is connected to a handle (not shown) or other actuating device, such as handle assembly 5 of FIG. 1, configured to actuate movement thereof within the lumen 206 of the inner shaft assembly 202.

To tension the sutures 212, 216, 220 and compress the stent frame 102', the wire 230 is retracted in a proximal direction. To allow the compressed stent frame 102' to expand, the wire 230 is moved distally to progressively release the tension in the sutures 212, 216, 220 thereby allowing the stent frame 102' to correspondingly self-expand into its natural state. To release the sutures 212, 216, 220 from the stent frame 102', the release pin 240 is pulled in the proximal direction such that the respective suture loops 215, 219, 223 disengage from the release pin 240. The sutures 212, 216, 220 are then pulled off of the stent frame 102' by proximal retraction of the wire 230.

Figure 6:
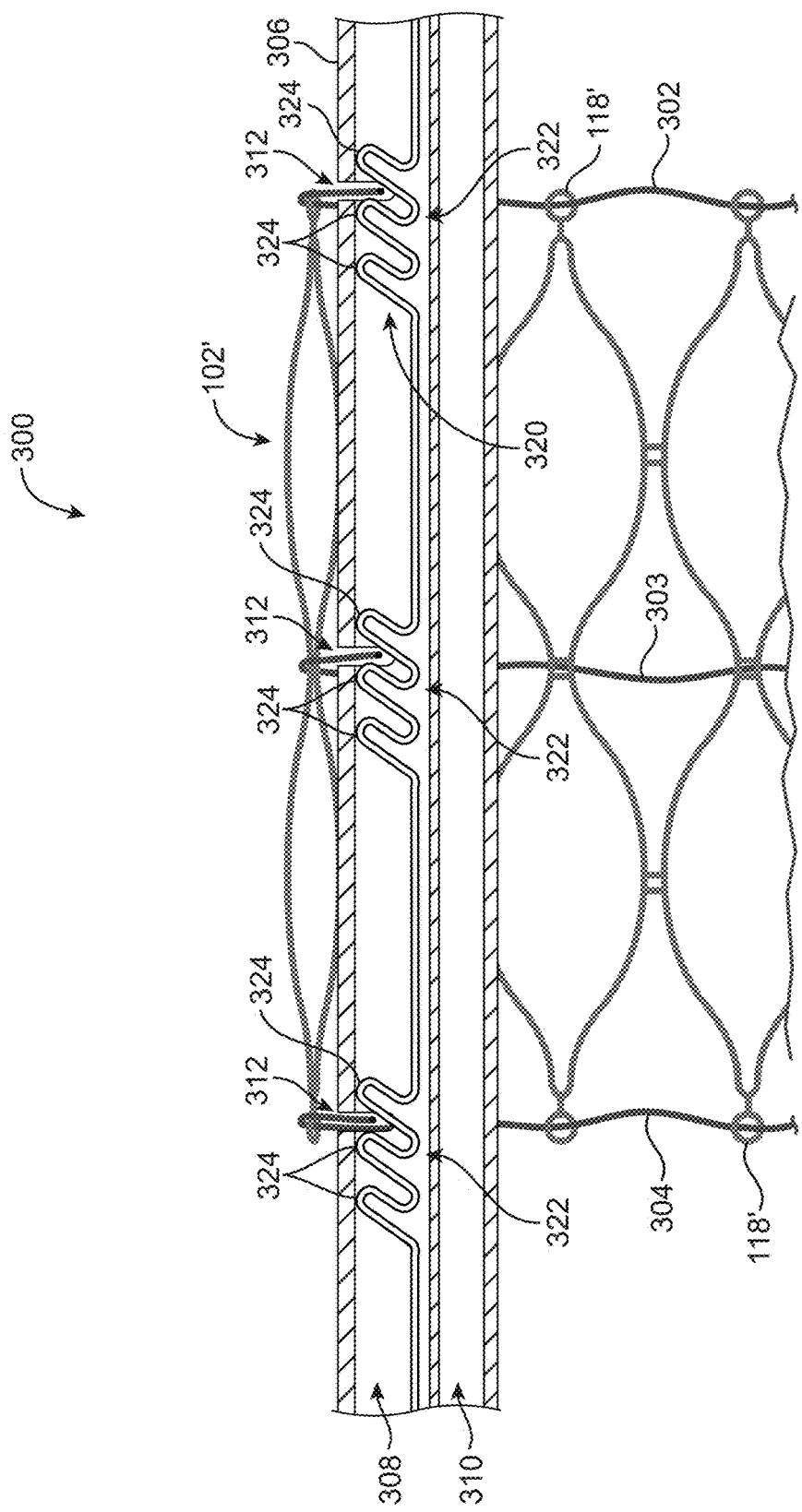
FIG. 6 is an exemplary suture actuation member placing tension in a suture positioned around the stented prosthetic heart valve of FIG. 4 (only the stent frame is shown for clarity).

FIG. 6 generally illustrates select components of one delivery device 300 and method for loading a prosthetic valve (only the stent frame 102' of the prosthetic valve is shown for ease of illustration). The stent frame 102' carries at least one suture (e.g., one proximal suture 302, one middle 303 suture and one distal suture 304) that is attached to the delivery device 300 for loading and delivery of the stent frame 102' to a defective heart valve. In this embodiment, the delivery device 300 controls the tension placed on the sutures 302-304, which form continuous loops or bands that remain with the valve frame 102' after deployment. The sutures 302-304 each form a loop having a diameter that is either equivalent or slightly larger than that of the prosthetic valve in its normal, expanded state. The delivery device 300 is similar to that of FIG. 1 and includes a catheter or inner shaft assembly 306, which can be used in place of the inner shaft assembly 4. The catheter 306 has a first lumen 308, a second lumen 310 and a plurality of access ports 312 fluidly in communication with the first lumen 308. A suture actuation member 320 is slidably disposed within the first lumen 308. The suture actuation member 320 includes a plurality of engagement sections 322, each engagement section 322 including at least one oval-shaped tooth 324. Alternatively, an entire length of the suture actuation member 320 can include the plurality of teeth 324. The more teeth 324 that are provided, the greater the opportunity for capturing the sutures 302-304 during a prosthetic valve loading procedure.

In operation, the sutures 302-304 can be secured through eyelets 118' or around the stent frame 102'. The stent frame 102' is threaded over the catheter 306 and positioned such that a segment of each of the sutures 302-304 is located within a respective one of the access ports 312. In this way, the sutures 302-304 are brought into engagement with a respective one of the teeth 324 in the corresponding access port 312. Once the sutures 302-304 are engaged with the suture actuation member 320, the suture actuation member 320 can be retracted proximally within the first lumen 308 of the catheter 306 to place tension in the sutures 302-304, and thus the stent frame 102', to compress the stent frame 102' from an expanded state into a loaded, compressed state for delivery via a patent's vasculature. Once delivered to the appropriate site, the actuation member 320 is moved distally such that tension in the sutures 302-304 is released, allowing the stent frame 102' to self-expand. Once the captured segments of the sutures 302-304 are brought into alignment with the respective access port 312, the sutures 302-304 disengage from respective teeth 324 to release the prosthetic valve from the delivery device 300. Movement of the suture actuation member 320 can be controlled with a handle assembly (not shown), such as the handle assembly 5 of FIG. 1. In this embodiment, the maximum height of the suture actuation member 320 is almost the same as the height of the first lumen 308 to prevent accidental disengagement of the sutures 302-304 when the sutures 302-304 are engaged with the teeth 324. While three sutures 302-304 are secured around the stent frame 102' in FIG. 6, it will be understood that the number and placement of the sutures 302-304 can vary.

Select components of a delivery device 400 utilizing the inner shaft assembly or catheter 306 and an alternate suture actuation member 420 are schematically illustrated in FIGS. 7A-7E. The suture actuation member 420 is made of a continuous wire form material and includes a plurality of generally sinuous engagement sections 422 in between straight portions 424. In the illustrated embodiment, the suture actuation member 420 includes three engagement sections 422, for the engagement of three respective sutures 302-304 carried by the stent frame 102' as described above. Alternatively, an entire length of the suture actuation member 420 includes the plurality of engagement sections 422. Each engagement section 422 includes a V-shaped section 426 leading to a generally sinuous-shaped section 428 that is arranged and configured to retain one suture 302-304 within a proximally slanted U-shaped retaining element or tooth 430. Following the generally sinuous-shaped section 428 is a ramp section 432 that leads to the following straight portion 424.

Figure 7A:
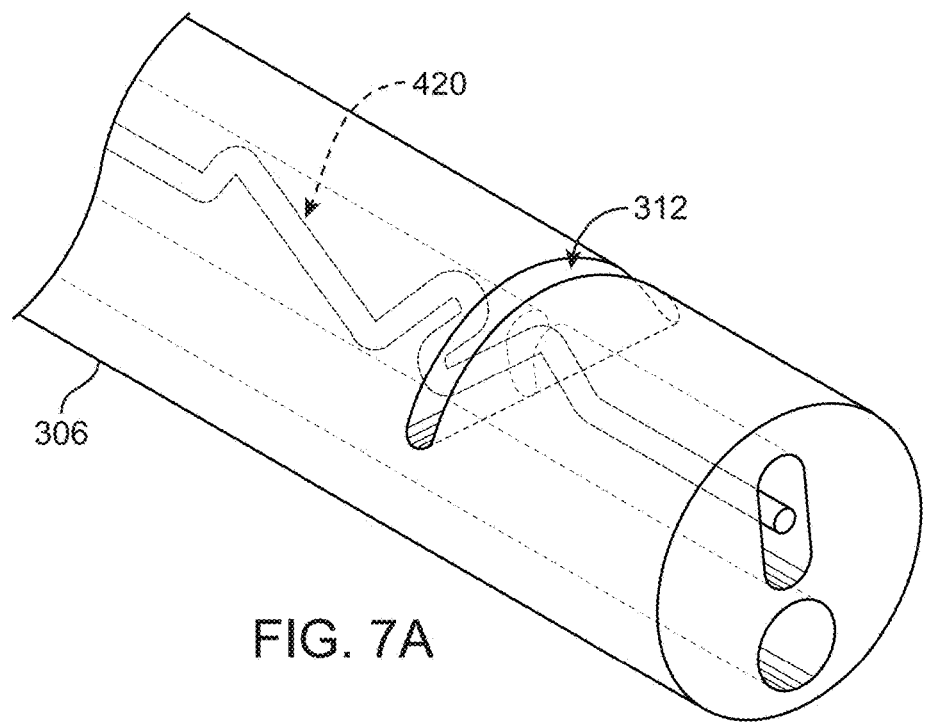
FIG. 7A is a perspective view of a suture actuation member, similar to that of FIG. 6, positioned within a catheter for loading of at least one suture (not shown).
Figure 7B:
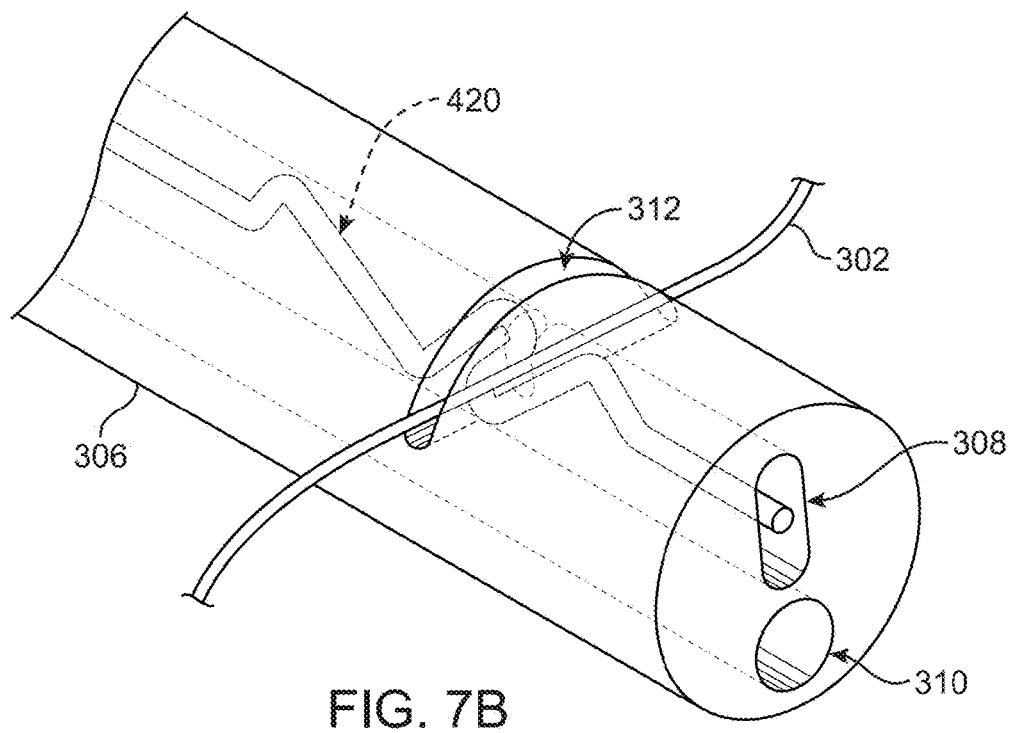
FIG. 7B is a partial, perspective view of the suture actuation member of FIG. 7A positioned within the catheter to tension the at least one suture.
Figure 7C:
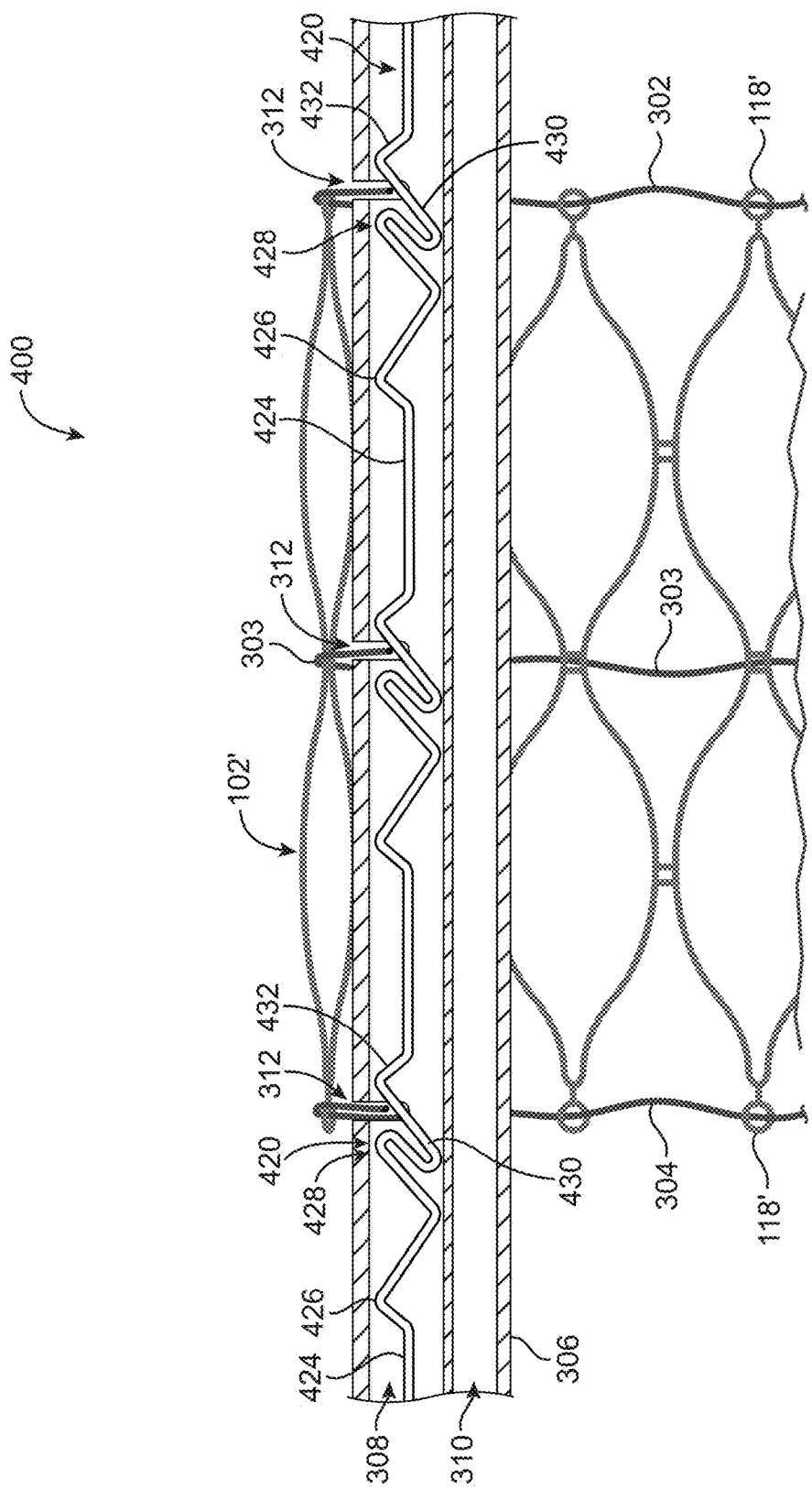
FIG. 7C is a partial, cross-sectional view of the suture actuation member of FIGS. 7A-7B positioned to release the at least one suture.
Figure 7D:
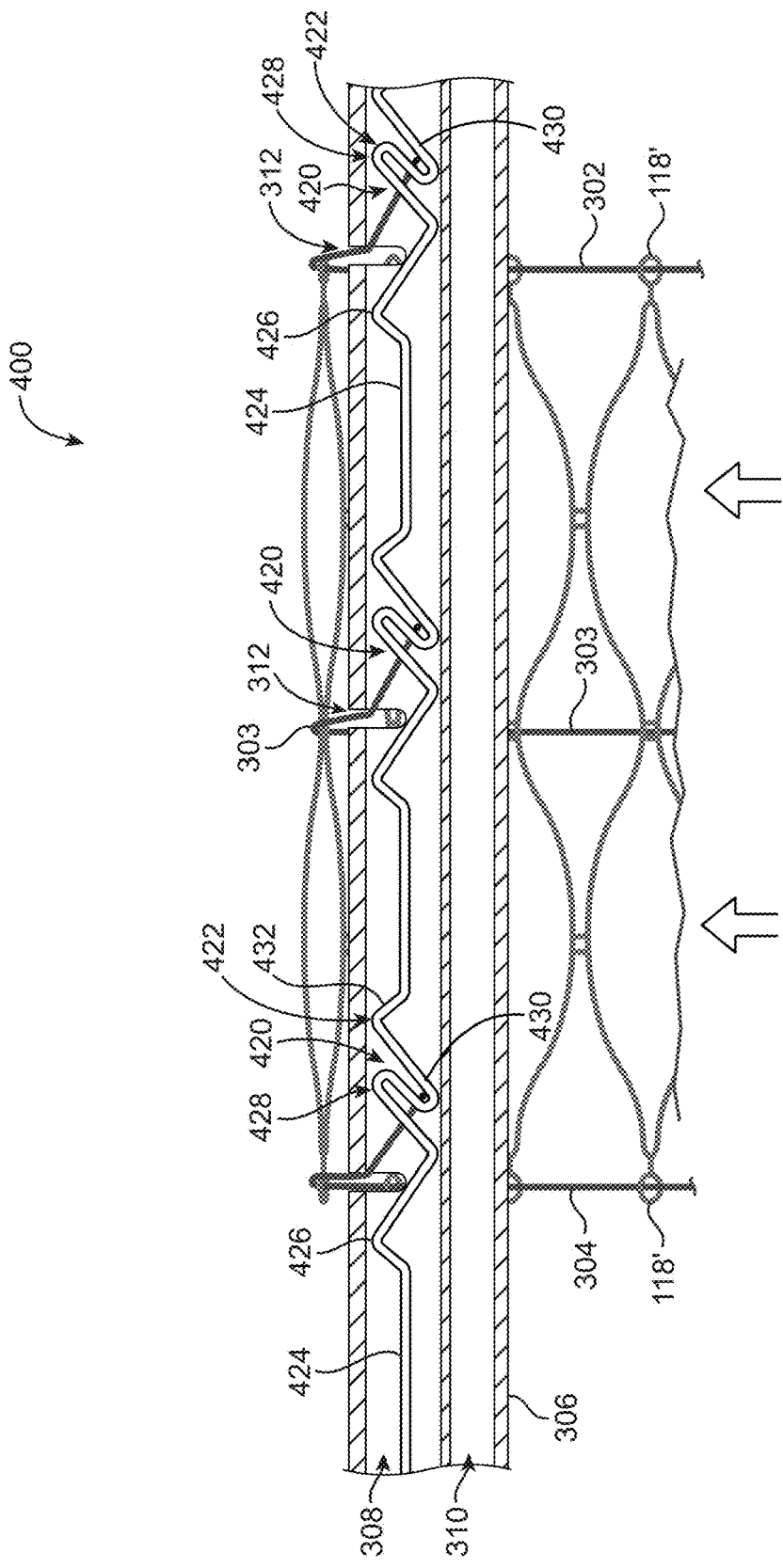
FIG. 7D is a partial, cross-sectional view of the suture actuation member of FIGS. 7A-7C having the sutures engaged to compress the stent frame.
Figure 7E:
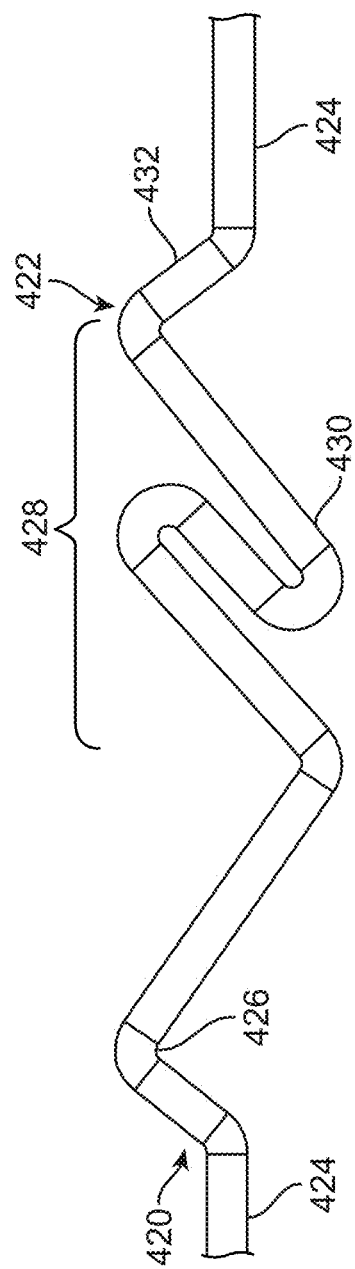
FIG. 7E is a partial, side view of the suture actuation member of FIGS. 7A-7D.

During loading of the prosthetic valve, the sutures 302-304 and engagement sections 422 are generally aligned with the access ports 312 in the catheter 306 such that the sutures 302-304 can be inserted within a respective access port 312 and engaged within one U-shaped retaining element 430 of one engagement section 422. Once the sutures 302-304 are engaged, the suture actuation member 420 is retracted proximally, relative to the catheter 306 as is generally illustrated in FIGS. 7C and 7D to place tension in the sutures 302-304 and subsequently compress the stent frame 102'. Once the prosthetic valve is at the target site and ready for deployment, the suture actuation member 420 is pushed distally such that the tension in the sutures 302-304 is relieved. As the actuation member 420 is moved distally from the retracted position of FIG. 7D to the position of FIG. 7C, the stent frame 102' compression from the sutures 302-304 is progressively relieved, thus slowly allowing the stent frame 102' to expand. The sutures 302-304 are released from the suture actuation member 420 when each suture passes the respective access port 312. In this embodiment, the sutures 302-304 remain with the stent frame 102' even after the catheter 306 and suture actuation member 420 are withdrawn from the patient. Movement of the suture actuation member 420 can be controlled with a handle assembly (not shown), such as handle assembly 5 of FIG. 1. While three sutures 302-304 are secured around the stent frame 102' in the present embodiment, it will be understood that the number and placement of the sutures 302-304 can vary.

Figure 8A:
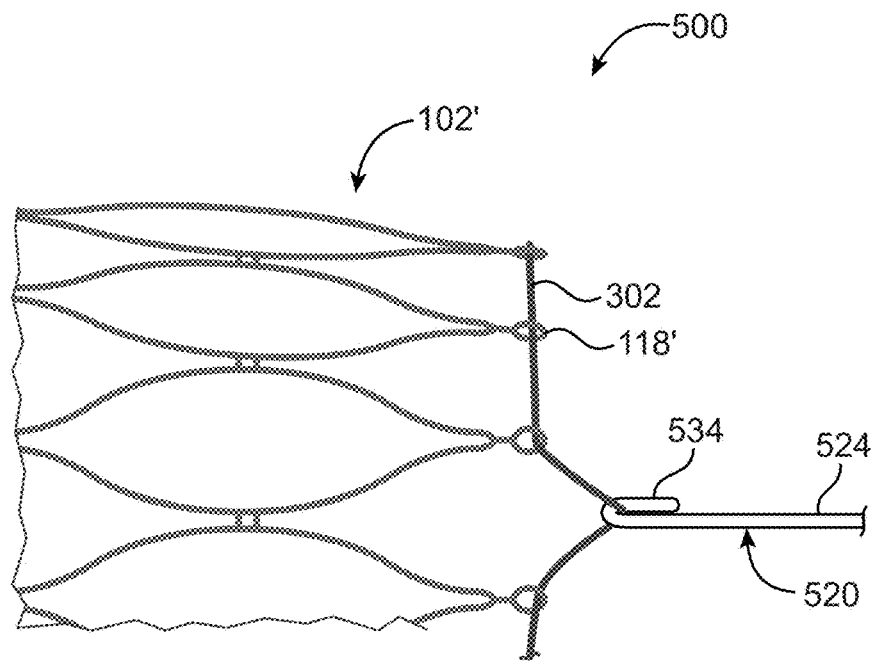
FIGS. 8A-8B are partial, side views of an alternate suture actuation member having a hook.
Figure 8B:
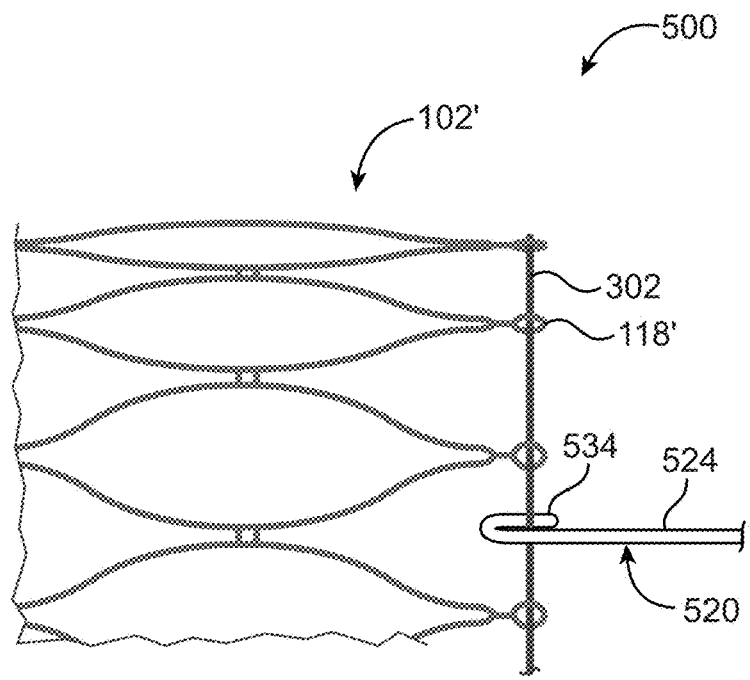

Select components of yet an alternate delivery device 500 are illustrated in FIG. 8A-8B. This delivery device 500 utilizes a suture actuation member 520 including a shaft 524 having at least one hook 534. As with the teeth or U-shaped retaining elements of the embodiments described above, the hook 534 operates in a similar manner to engage and disengage at least one suture 302. Suture actuation member 520 can optionally include a plurality of spaced-apart hooks for engaging multiple sutures. As with prior embodiments, movement of the suture actuation member 520 can be controlled with a handle assembly (not shown), such as handle assembly 5 of FIG. 1. Furthermore, the suture actuation member 520 can be positioned within or positioned alongside a catheter or inner shaft assembly, such as that disclosed with respect to prior embodiments.

Although the present disclosure has been described with reference to preferred embodiments, workers skilled in the art will recognize that changes can be made in form and detail without departing from the spirit and scope of the present disclosure.

What is claimed is:

1. A method of adjusting the expansion and contraction of a prosthetic heart valve prior to deployment, the method comprising the steps of:
   providing a prosthetic heart valve;
   providing a suture positioned around the prosthetic heart valve, the suture having a first end and a second end;
   providing a catheter having a lumen and a slot transversely positioned with respect to the lumen;
   providing a release pin within the lumen, the first end of the suture connected to the release pin;
   providing a wire within the lumen, the second end of the suture connected to the wire;
   loading the prosthetic heart valve onto the wire and release pin to form a sub assembly and then inserting the sub assembly through the slot and into the lumen; and
   pulling the wire to place tension in the suture to correspondingly compress the prosthetic heart valve.

2. The method of claim 1, wherein the step of providing a suture comprises providing a plurality of sutures each having first and second ends, wherein the first end of each suture is connected to the release pin and the second end of each suture is connected to the wire.

3. The method of claim 2, further comprising the step of providing two position stabilizers positioned on the wire for each of the plurality of sutures; wherein the position stabilizers collectively maintain a longitudinal position of each of the plurality of sutures with respect to the wire.

4. The method of claim 1, wherein movement of second end of the suture is longitudinally restrained with respect to the wire.

5. The method of claim 4, wherein the second end of the suture is tied to the wire.

6. The method of claim 4, wherein the wire includes a plurality of position stabilizers to restrain movement of the second end of the suture.

7. The method of claim 1, further comprising the step of proximally retracting the release pin to disengage the release pin from the suture and proximally retracting the wire to disengage the suture from the prosthetic heart valve.

8. The method of claim 1, wherein the first end of the suture includes a loop through which the release pin is threaded.

9. The method of claim 1, wherein the prosthetic heart valve includes an eyelet and the suture is threaded through the eyelet.

10. A combination delivery device and prosthetic heart valve, the combination comprising:
a prosthetic heart valve having a stent frame and a suture positioned around the stent frame, the suture including a first end and a second end; and
a delivery device including:
a catheter having a lumen and a slot transversely positioned with respect to the lumen, the slot sized to receive the prosthetic heart valve therein,
a release pin positioned within the lumen, the first end of the suture connected to the release pin;
a wire positioned within the lumen, the second end of the suture connected to the wire; and
wherein the wire can be pulled proximally to place tension in the suture and correspondingly compress the prosthetic heart valve.

11. The combination of claim 10, further comprising a plurality of sutures each having first and second ends, wherein the first end of each suture is connected to the release pin and the second end of each suture is connected to the wire.

12. The combination of claim 10, wherein movement of second end of the suture is longitudinally restrained with respect to the wire.

13. The combination of claim 12, wherein the second end of the suture is tied to the wire.

14. The combination of claim 12, wherein the wire includes a plurality of position stabilizers to restrain movement of the second end of the suture.

15. The combination of claim 10, wherein the first end of the suture includes a loop through which the release pin is threaded.

16. The combination of claim 10, further comprising a plurality of sutures, wherein each suture is the same length.

* * * * *